United States Patent
Raines, Jr. et al.

(10) Patent No.: US 7,185,562 B2
(45) Date of Patent: Mar. 6, 2007

(54) DISPOSABLE BATTERY POWERED SCREW DRIVER, LOCKING MECHANISM, AND ACCESSORIES

(75) Inventors: Aaron T. Raines, Jr., Dallas, TX (US); Shaher A. Ahmad, Plano, TX (US)

(73) Assignee: OsteoMed L.P., Addison, TX (US)

( * ) Notice: Subject to any disclaimer, the term of this patent is extended or adjusted under 35 U.S.C. 154(b) by 0 days.

(21) Appl. No.: 11/006,977

(22) Filed: Dec. 8, 2004

(65) Prior Publication Data

US 2006/0117911 A1    Jun. 8, 2006

(51) Int. Cl.
*B25B 13/00* (2006.01)
*B25B 21/00* (2006.01)
*B25B 23/00* (2006.01)
*B25B 23/151* (2006.01)

(52) U.S. Cl. ............... 81/52; 81/429; 81/469

(58) Field of Classification Search ............. 81/52, 81/429, 469, 475, 58.3; 408/241; 173/178
See application file for complete search history.

(56) References Cited

U.S. PATENT DOCUMENTS

| | | | | |
|---|---|---|---|---|
| 4,154,308 A | * | 5/1979 | Goldsberry et al. | 173/178 |
| 4,875,612 A | * | 10/1989 | Lee | 227/147 |
| 4,878,404 A | * | 11/1989 | Liao | 81/54 |
| 5,643,533 A | * | 7/1997 | Fishman | 422/1 |
| 5,690,577 A | * | 11/1997 | Enzmann et al. | 475/265 |
| 5,881,613 A | * | 3/1999 | Han | 81/429 |
| 6,329,778 B1 | * | 12/2001 | Culp et al. | 318/434 |
| D474,086 S | * | 5/2003 | Heun | D8/61 |
| 6,592,040 B2 | * | 7/2003 | Barkan et al. | 235/472.01 |
| D487,383 S | * | 3/2004 | Ng | D8/61 |

* cited by examiner

*Primary Examiner*—Lee D. Wilson
*Assistant Examiner*—Alvin J. Grant
(74) *Attorney, Agent, or Firm*—Baker Botts L.L.P.

(57) ABSTRACT

In accordance with one embodiment of the present invention, a driver may include an electric motor coupled to a bit interface. The bit interface may include a generally cylindrical body having first and second hollow portions. The first hollow portion may be on one end of the generally cylindrical body and may define a generally cylindrical hole. The second hollow portion may abut the first hollow portion and define an oblong channel. The oblong channel may be further defined by first and second parallel flat walls. The cylindrical body may also include a first transverse groove.

20 Claims, 3 Drawing Sheets

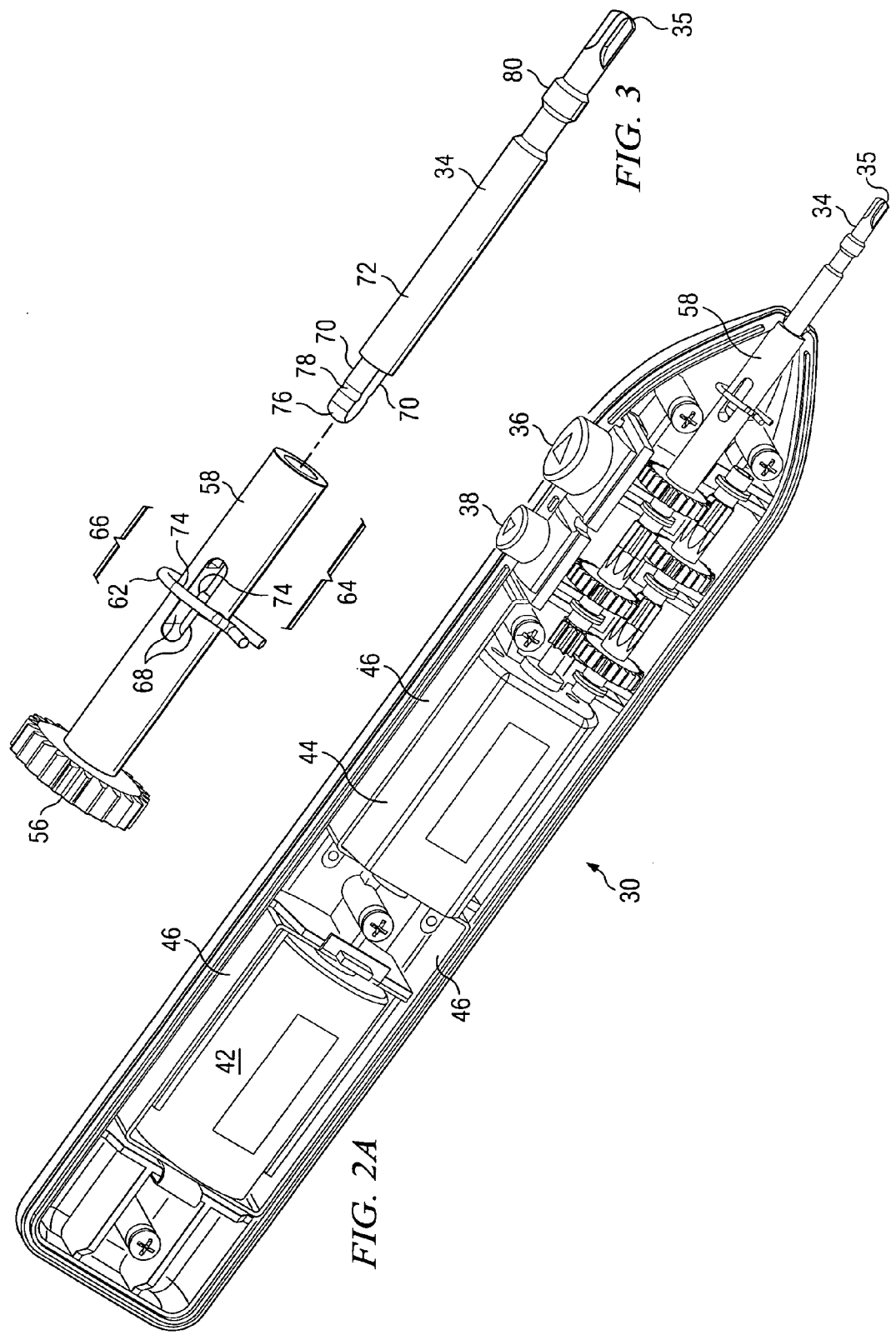

DISPOSABLE BATTERY POWERED SCREW DRIVER, LOCKING MECHANISM, AND ACCESSORIES

TECHNICAL FIELD OF THE INVENTION

The present invention relates generally to disposable surgical tools and more particularly to a disposable battery powered screw driver, locking mechanism and accessories.

BACKGROUND OF THE INVENTION

Many different tools are used during surgical procedures to facilitate different aspects of the procedures. A commonality to all surgical tools is that they should be sterilized prior to use during a surgical procedure to minimize the chance of patient infection. The health care industry expends a considerable amount of time and money to perform these sterilizations. In the case of many surgical tools, the tools are shipped sterile from the manufacturer. If these tools are designed to be reusable, the tools will require resterilization following use. These resterilizations can be performed by the hospital, or the tools may be returned to the manufacturer for resterilization. In either case, an additional expense is incurred by the need to maintain sterilization equipment and personnel trained in its use, or by additional shipping and transaction costs.

Sterilization concerns are magnified for battery powered power tools as there are additional concerns about battery life and/or recharging the battery. Starting a procedure with a partially charged tool runs the risk that the tool battery may not last for the entire procedure. Therefore, a sterile charging environment may be required, or the tools may need to be recharged prior to sterilization. This increases the tool's down time and requires that a hospital keep extra tools on hand. The extra tools must also be maintained and kept sterile, once again increasing costs

SUMMARY OF THE INVENTION

In accordance with the teachings of the present invention, the disadvantages and problems associated with surgical power tools have been substantially reduced or eliminated. In particular, the system and method described herein provide for single use drivers that reduce or eliminate the need for resterilization procedures and may be relied upon to last through a procedure.

In accordance with one embodiment of the present invention, a driver may include an electric motor coupled to a bit interface. The bit interface may include a generally cylindrical body having first and second hollow portions. The first hollow portion may be on one end of the generally cylindrical body and may define a generally cylindrical hole. The second hollow portion may abut the first hollow portion and define an oblong channel. The oblong channel may be further defined by first and second parallel flat walls. The cylindrical body may also include a first transverse groove.

The driver may also include a retaining clip seated in the first transverse groove and operable to secure a driver bit in the bit interface. The electric motor and the bit interface may be at least partially surrounded by a plastic housing. The driver may also include a battery operable to power the electric motor, and a flex circuit operable to electrically couple the electric motor to the battery. The driver may also utilize a gear reduction process to translate the angular velocity generated by the electric motor into torque. At least one plastic gear may be used.

In accordance with another embodiment of the present invention, a driver may include a bit interface coupled to a driver bit, and a retaining clip coupled to both the bit interface and the driver bit. The bit interface may include a generally cylindrical body having first and second hollow portions. The first hollow portion may be on one end of the generally cylindrical body and define a generally cylindrical hole. The second hollow portion may abut the first hollow portion and define an oblong channel. The oblong channel may be further defined by first and second parallel flat walls. The cylindrical body also includes a transverse groove. The driver bit may include a cylindrical shaft with a screw head interface on one end and an anti-rotation interface on the other end. The anti-rotation interface may include first and second parallel flats. The cylindrical shaft may also include a retention groove. The first and second flats may be disposed between the first and second flat walls and a portion of the cylindrical shaft proximate the first and second flats may be disposed within the first hollow portion. The transverse groove may align with the retention groove and the retaining clip may be at least partially disposed within the transverse groove and the retention groove.

Technical advantages of certain embodiments of the present invention include a surgical driver which is inexpensive to replace and designed to be disposed of after use. This eliminates the need for the hospital to resterilize the driver for another procedure. The driver is manufactured from inexpensive parts, and is therefore inexpensive to replace after each procedure. Therefore, it is cost effective for hospitals to dispose of the driver following its use, rather than attempting to resterilize and reuse the driver.

Another technical advantage of certain embodiments of the present invention is a disposable surgical driver containing a battery with sufficient power to last for at least the duration of one surgical procedure. This eliminates concerns of a battery having insufficient charge during a procedure to complete the procedure.

A further technical advantage of certain embodiments of the present invention is a driver utilizing a gear reduction mechanism. By using gear reduction, the power requirements of the driver motor may be reduced. This allows for a smaller and lower voltage battery to be used. The battery life, and thereby the tool life, may also be extended.

Other technical advantages of the present invention will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

FIGS. 2A and 2B illustrate the driver of FIG. 1 with a portion of the housing removed; and FIG. 3 illustrates the bit retention system and driver bit of FIG. 1.

DETAILED DESCRIPTION OF THE INVENTION

Figure 1:
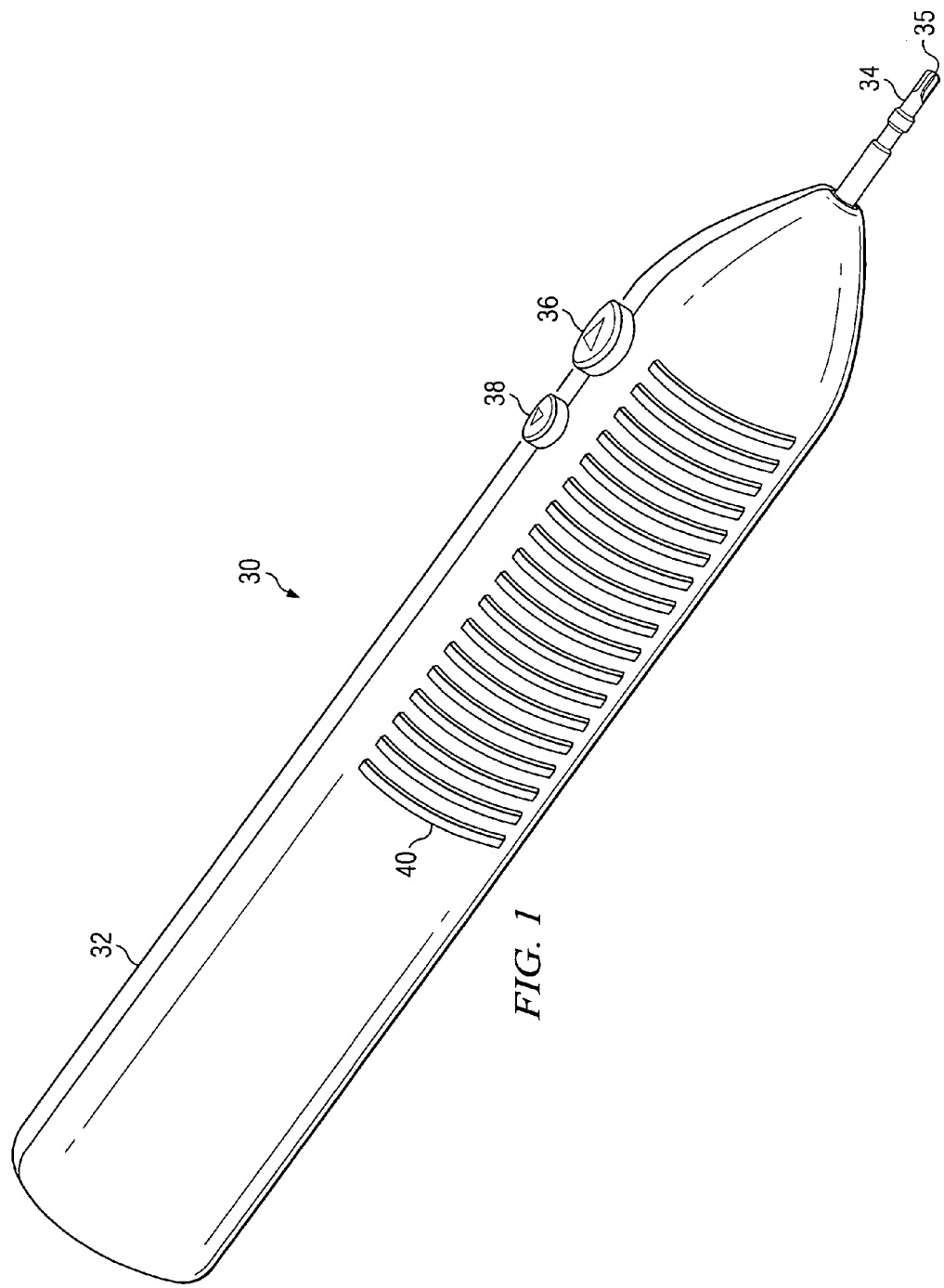
FIG. 1 illustrates one embodiment of a disposable driver in accordance with the present invention.

FIG. 1 illustrates a disposable driver 30 for use in surgical procedures. Driver 30 is designed to be inexpensive to manufacture, and therefore inexpensive to replace for each surgical procedure.

Disposable surgical tools are desirable because tools used in surgery must be sterilized. Many tools used in surgical procedures are sterilized prior to shipping from the manufacturer and are packaged to maintain the tool's sterility. If surgical tools are to be reused, then hospitals must invest in equipment and employee time to perform the sterilizations. Further, sterilization techniques may involve high temperatures or harsh chemicals, and tools intended to be resterilized would need to be capable of withstanding the sterilization conditions while maintaining their functionality.

In the specific instance of power tools, rechargeable batteries degrade over the life of the tools. As a tool gets older, the battery lasts for a continuously decreasing time period. Sterilization procedures may also reduce battery life. In addition, these tools typically require the intervention of a person to recharge them. The combination of human error in forgetting to charge the battery of a tool, with mechanical error caused by an aging battery, may result in failure of a tool during a surgical procedure. Stopping a surgical procedure to secure another tool is not desirable. Neither is maintaining backup tools in the event of tool failure. For at least these reasons, it is desirable to have inexpensive surgical tools which do not require resterilization or recharging following a surgical procedure, and have sufficient power to last for an entire procedure. Driver 30 is designed to meet these requirements.

In one embodiment, the driver housing may be made of a commercial grade plastic, such as polycarbonate/polyester. This plastic is cost effective for a single use device, but does not hold up well to the high temperature and high moisture that is associated with repeated autoclaving (sterilization). A plastic may be used to manufacture the gears and bearings, such as straight and glass filled nylon. These plastics also do not hold up well to the moisture, without swelling, associated with repeated autoclaving. Devices designed to survive repeated autoclaving might need to be made from more costly materials such as aluminum, stainless steel, or high temperature, low moisture absorbing plastics such as Radel, Ultem or other more expensive plastics.

The driver battery may be a low cost non-rechargeable lithium type battery that loses at least half of its energy when autoclaved one time. The driver motor may be an inexpensive DC motor like those found in retail battery powered devices like electric shavers, powered screwdrivers or motor driven toys. The driver motor is not designed to survive autoclaving because it is constructed out of carbon steels that may rust, and plastics that cannot hold up to the high temperature and moisture that are common with autoclaving.

Reusable tools present the problem of cleaning tool crevices, and the sterility of autoclaved power tools may be questionable. Reusable power tools may also break down from repeated use and repeated autoclaving. If a tool breaks down in the middle of a procedure, a replacement has to be found and sterilized to finish the procedure. Issues also arise from battery powered devices which include autoclavable batteries that loose energy when autoclaved. Hospital billing may also be simplified by using a single use device as a single patient may be billed for the tool rather than attempting to capitalize the cost of a reusable tool over the number of procedures in which it is expected to be used.

In the illustrated embodiment, driver 30 includes a two-piece housing 32. The two halves of housing 32 may be snapped together, held together by screws, held together by epoxy, or held together by another appropriate mechanism. In an alternative embodiment, housing 32 could include more than two pieces held together in any appropriate manner.

Coupled to the front of driver 30 is bit 34. In the illustrated embodiment, bit 34 includes a rotational interface 35 that is configured to interface with a Phillips head screw. Alternative embodiments of bit 34 may include a rotational interface 35 configured to interface with taps, drill bits, adaptors, or other screw types such as flat head, Allen, Torx, square, or other screw head configurations. Alternatively, rotational interface 35 may not be configured to interface with a screw head, but may be configured to interface with a nut, such as a hex nut, or may be configured to receive a driver bit, or drill a hole through material such as bone.

Bit 34 may be rotated by pressing forward button 36 or reverse button 38. Driver 30 is configured such that pressing reverse button 38 causes bit 34 to rotate in the opposite direction as it would if forward button 36 were pressed. By pressing forward button 38 a screw may be installed or a hole may be drilled. By pressing reverse button 38 a screw may be removed or a bit may be withdrawn. Forward button 36 and reverse button 38 may be made from a flexible material such as rubber, or they may be made from a rigid material such as a hard plastic.

In the illustrated embodiment, driver 30 includes ridges 40 on housing 32. These ridges may be incorporated to improve the gripping surface of driver 30 and to prevent slippage or loss of grip on driver 30. Alternative embodiments could improve the grip on driver 30 in many different ways, for example, by including knurling, heavy texturing, or providing protrusions to prevent slipping.

Figure 2B:
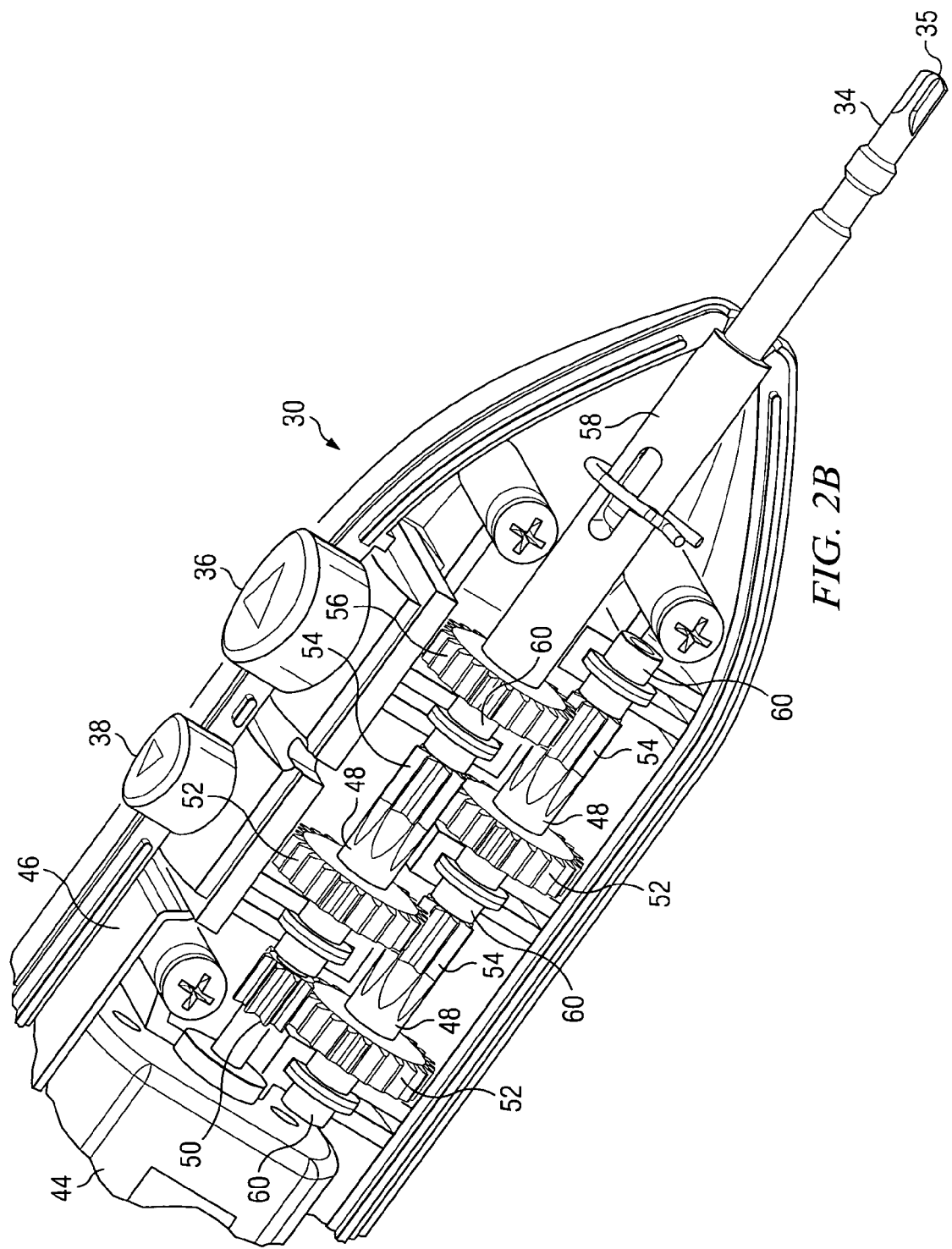

FIGS. 2A and 2B illustrate driver 30 with one half of housing 32 removed. Forward button 36 and reverse button 38 are shown electrically coupled to battery 42 and motor 44. In the illustrated embodiment, the electrical coupling is provided by circuit board 46. circuit board 46 may be a nonconductive material that has an electrical circuit disposed on or within it. In alternative embodiments, the electrical coupling of the components of driver 30 could be accomplished using a flex circuit with an electrical circuit disposed on or within it, or by traditional wires. In one embodiment, a flex circuit may be used which is made of a flooded single sided 2 oz copper etch on a polyimide substrate. The single sided circuit is inexpensive, and the flooded 2 oz copper etch provides adequate current carrying ability and low voltage drop. Alternative embodiments of driver 30 may use multi-layer flex circuits, silver ink etch, or substrates such as polyesters. Further alternative embodiments may utilize metal strips or discrete wires.

Battery 42 could be any type of battery capable of supplying motor 44 with its required voltage and current. In one embodiment, motor 44 may operate on 3 volts DC. In alternative embodiments, motor 44 may operate on any desired voltage and current. Battery 42 would have a corresponding voltage range and be capable of providing this voltage for at least the entire designed life of driver 30 (e.g., for the duration of one surgical procedure).

In the illustrated embodiment, motor 44 does not need to be a high powered motor or even be capable of providing sufficient torque to install a screw or drive a driver bit. This is true because motor 44 does not directly drive bit 34, but transmits the drive forces through a set of transmission gears 48. Transmission gears 48 utilize a gear-reduction technique to translate angular velocity into torque.

Motor 44 is coupled to and turns drive gear 50. Drive gear 50 then turns the first transmission gear 48. Transmission gears 48 include a large gear 52 and a small gear 54. Large gear 52 and small gear 54 are coupled such that they turn as one unit. Drive gear 50 turns the first large gear 52. This also causes the first small gear 54 to turn at the same rate as the first large gear 52. First small gear 54 interfaces with and turns the second large gear 52. In this manner, the second large gear 52 is turning more slowly, i.e. has less angular velocity, than the first large gear 52, but the second large gear 52 is turning with more torque than the first large gear 52. This gear-reduction technique may be used as many times as is desired to translate the angular velocity of drive gear 50 into the desired torque at bit 34. In the illustrated embodiment, three stages of gear reduction are utilized, as evidenced by the three transmission gears 48. In alternative embodiments, any number of gear reduction steps could be utilized, or motor 44 could directly drive bit 34.

The small gear 54 of the final transmission gear 48 is coupled to and turns interface gear 56. Interface gear 56 is coupled to bit interface 58 in such a manner that bit interface 58 turns when interface gear 56 is turned. Bit 34 is also securely fixed to bit interface 58 such that bit 34 turns when bit interface 58 is turned. In this manner, motor 44 is capable of driving bit 34. Each side of the transmission gears 48 and one side of interface gear 56 are supported by bearings 60. Though some of these components share bearings 60, the components are not connected through the bearings 60 and are therefore free to spin at different angular velocities.

Transmission gears 48 may be cut or cast from a single material as one piece units, or large gears 52 may be separate pieces of the same or different material as small gears 54. In a like manner, interface gear 56 and bit interface 58 may be cut or cast from a single material as one piece units, or interface gear 56 may be a separate piece of the same or different material as bit interface 58.

FIG. 3 is an enlarged view illustrating bit 34 decoupled from bit interface 58. Bit interface 58 and bit 34 are designed to have corresponding features such that they fit together and may be securely coupled. Further, retaining clip 62 is coupled to both bit interface 58 and bit 34 and serves to further secure the two pieces together.

Bit interface 58 has a generally cylindrical shape, however, portions of bit interface 58 have been hollowed to accept bit 34. A first portion 64 of bit interface 58 has had its center portion removed such that a hollow cylinder or tube remains. The hole created in first portion 64 by the removal of it center portion is sized to be slightly larger than shank 72 of bit 34. This allows shank 72 of bit 34 to be inserted into the end of bit interface 58.

Abutting first portion 64, a second portion 66 has had an oblong section removed such that an oblong hole passes from one side of bit interface 58 to the other. The removal of the oblong section of second portion 66 leaves two parallel flat walls 68. Flat walls 68 interface with flats 70 on bit 34 and the combination keeps bit 34 from rotating independently from bit interface 58.

Second portion 66 may abut or overlap first portion 64 such that the oblong hole cut from second portion 66 intersects the hole in first portion 64. This allows bit 34 to be inserted into bit interface 58 such that flats 70 interface with flat walls 68 and the portion of shank 72 immediately beyond flats 70 interfaces with the hole in first portion 64. The remainder of bit 34 protrudes from the front of bit interface 58 and driver 30.

Retaining clip 62 keeps bit 34 from falling out of bit interface 58. Retaining clip 62 is seated in grooves 74 cut into bit interface 58. As bit 34 is inserted into bit interface 58, the arms of retaining clip 62 are forced apart by rounded end 76 on bit 34. Bit 34 is pushed into bit interface 58 until the arms of retaining clip 62 close over grooves 78 on bit 34. When installed in this manner, retaining clip 62 is seated in grooves 74 on bit interface 58 and grooves 78 on bit 34 and holds bit 34 securely within bit interface 58.

Retaining clip 62 is illustrated as having two relatively straight arms joined by an arcuate section. One of the arms includes a bent section which faces the other arm and prevents retaining clip 62 from slipping off of bit interface 58. In the illustrated embodiment, each of the arms of retaining clip 62 are seated in a groove 74 and a groove 78. Alternative embodiments may use retaining clips of many different shapes such as a clip with an arcuate arm and a straight arm. In some such embodiments, only one of the arms may be seated in a groove on the bit interface and a groove on the bit. Other alternative embodiments could include a bent section on each arm to prevent the retaining clip from slipping off of the bit interface. In further alternative embodiments, any shape of retaining clip 62 capable of securing bit 34 in bit retainer 58 may be used.

The force required to insert or remove bit 34 from bit interface 58 may be adjusted by changing the design of retaining clip 62. For instance, in the illustrated embodiment, retaining clip 62 is formed from a round piece of metal stock. The strength of retaining clip 62, and therefore the force required to separate the arms of retaining clip 62, could be increased by increasing the diameter of the metal stock used to form retaining clip 62. In alternative embodiments, retaining clip 62 could be formed from metal with cross sections that are not round, or may be formed from round or non-round non-metals.

In the illustrated embodiment, grooves 74 are located in second portion 66 and grooves 78 are placed correspondingly. In alternative embodiments, grooves 74 and 78 may be placed at nearly any point along first portion 64 or second portion 66 to change the position of retaining clip 62.

During a surgical procedure, it may be desirable to change bit 34 from one type of bit to another. For instance, a surgeon may wish to change from a drilling bit to a bit with a Phillips head screw driver. In the illustrated embodiment, bit 34 contains a ridge 80 which may be used to facilitate removing bit 34 from bit interface 58. Ridge 80 provides an increased diameter surface which can be pulled on to remove bit 34. Alternative embodiments may place ridge 80 in a different spot on shank 72, may use alternative grip enhancing features, or may not include any grip enhancing features. In an alternative embodiment, ridge 80 or the trough formed on either side of ridge 80 may be painted, or otherwise color coded with a color or symbol indicating the type or size of bit 34. In this embodiment, bits may be easily interchanged without needing to examine the end of the drill bit or look for small etchings on the side of the bit to ensure the bit is the desired bit.

Although the present invention has been described in several embodiments, a myriad of changes and modifications may be suggested to one skilled in the art, and it is intended that the present invention encompass such changes and modifications as fall within the scope of the present appended claims.

What is claimed is:
1. A driver, comprising:
an electric motor; and
a bit interface coupled to the electric motor, the bit interface including:
a generally cylindrical body defining a longitudinal bore extending from a first end of the cylindrical body to a central portion of the cylindrical body;

wherein the central portion of the cylindrical body defines an oblong channel that extends radially through the cylindrical body and the longitudinal bore;

wherein the oblong channel is further defined by:

a first flat wall; and a second flat wall generally parallel to the first flat wall; and the central portion of the cylindrical body further defining a first transverse groove adjacent the oblong channel and extending generally perpendicular to the longitudinal bore.

2. The driver of claim 1, further comprising a retaining clip operable to secure a driver bit in the bit interface and wherein the retaining clip is coupled to the generally cylindrical body and seated in the first transverse groove.

3. The driver of claim 2, wherein the force required to remove the driver bit from the bit interface is determined by the diameter of the retaining clip.

4. The driver of claim 2, further comprising:

the central portion of the cylindrical body further defining a second transverse groove adjacent the oblong channel and extending generally perpendicular to the longitudinal bore;

the second transverse groove being generally parallel to the first transverse groove; and the retaining clip being seated in the second transverse groove.

5. The driver of claim 1, further comprising a plastic housing at least partially enclosing the electric motor and the bit interface.

6. The driver of claim 1, further comprising a battery operable to power the electric motor.

7. The driver of claim 6, further comprising a flex circuit operable to electrically couple the electric motor to the battery.

8. The driver of claim 1, wherein the electric motor is operable to turn the bit interface in a direction selected from the group consisting of clockwise and counter-clockwise.

9. The driver of claim 8, wherein the direction that the bit interface is turned is selected by depressing a forward button or a reverse button.

10. The driver of claim 1, further comprising a plurality of dissimilarly sized gears, and wherein the angular velocity generated by the electric motor is translated into torque by a gear-reduction process.

11. The driver of claim 1, further comprising the electric motor being coupled to the bit interface by a plurality of gears.

12. The driver of claim 11, wherein at least one of the plurality of gears comprises a plastic gear.

13. A driver bit retainer, comprising:

a generally cylindrical body defining a longitudinal bore extending from a first end of the cylindrical body to a central portion of the cylindrical body;

wherein the central portion of the cylindrical body defines an oblong channel that extends radially through the cylindrical body and the longitudinal bore;

wherein the oblong channel is further defined by:

a first flat wall; and a second flat wall generally parallel to the first flat wall; and the central portion of the cylindrical body further defining a first transverse groove adjacent the oblong channel and extending generally perpendicular to the longitudinal bore.

14. The driver bit retainer of claim 13, further comprising:

the central portion of the cylindrical body further defining a second transverse groove adjacent the oblong channel and extending generally perpendicular to the longitudinal bore; and the second transverse groove being generally parallel to the first transverse groove.

15. The driver bit retainer of claim 14, wherein the first transverse groove and the second transverse groove are perpendicular to a longitudinal axis of the generally cylindrical body.

16. The driver bit retainer of claim 14, wherein the first transverse groove and the second transverse groove intersect the oblong channel.

17. A driver, comprising:

an electric motor;

a battery electrically coupled to the electric motor;

a bit interface coupled to the electric motor by a plurality of transmission gears;

wherein the plurality of transmission gears are operable to translate the angular velocity generated by the electric motor into torque;

wherein the bit interface includes:

a generally cylindrical body defining a longitudinal bore extending from a first end of the cylindrical body to a central portion of the cylindrical body;

an interface gear coupled to a first end of the generally cylindrical body, the interface gear operable to interface with at least one of the plurality of transmission gears;

wherein the central portion of the cylindrical body defines an oblong channel that extends radially through the cylindrical body and the longitudinal bore;

wherein the oblong channel is further defined by:

a first flat wall; and a second flat wall generally parallel to the first flat wall;

the central portion of the cylindrical body further defining first and second transverse grooves adjacent the oblong channel and extending generally perpendicular to the longitudinal bore;

wherein the first transverse groove is generally parallel to the second transverse groove;

wherein the first and second transverse grooves are on opposite sides of the generally cylindrical body; and wherein the first and second transverse grooves each intersect the oblong channel;

a retaining clip coupled to the generally cylindrical body and operable to secure a driver bit in the bit interface;

wherein the retaining clip is seated in the first and second transverse grooves; and a plastic housing at least partially enclosing the electric motor, the battery, the bit interface, and the plurality of transmission gears.

18. A method, comprising:

coupling an electric motor to a bit interface such that the bit interface turns when the electric motor is activated;

wherein the bit interface includes:

a generally cylindrical body defining a longitudinal bore extending from a first end of the cylindrical body to a central portion of the cylindrical body;

wherein the central portion of the cylindrical body defines an oblong channel that extends radially through the cylindrical body and the longitudinal bore;

wherein the oblong channel is further defined by:

a first flat wall; and a second flat wall generally parallel to the first flat wall; and the central portion of the cylindrical body further defining a transverse groove adjacent the oblong channel and extending generally perpendicular to the longitudinal bore.

19. The method of claim 18, further comprising:

sterilizing the bit interface and electric motor;

sealing a package that encloses the bit interface and electric motor after sterilizing the bit interface and electric motor;

shipping the bit interface and electric motor after sealing the package.

20. The method of claim 18, further comprising coupling a bit to the bit interface by inserting a back end of the bit into the bit interface until a retaining clip seated in the transverse groove engages a retention groove on the bit.

* * * * *